(12) United States Patent
Radman (10) Patent No.: US 9,782,129 B2
(45) Date of Patent: Oct. 10, 2017

(54) PRESSURE SENSING GUIDEWIRES

(71) Applicant: BOSTON SCIENTIFIC SCIMED, INC., Maple Grove, MN (US)

(72) Inventor: Lloyd Radman, Blaine, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 147 days.

(21) Appl. No.: 14/814,500

(22) Filed: Jul. 30, 2015

(65) Prior Publication Data

US 2016/0029961 A1    Feb. 4, 2016

Related U.S. Application Data

(60) Provisional application No. 62/032,169, filed on Aug. 1, 2014.

(51) Int. Cl.
*A61B 5/00* (2006.01)
*A61B 5/0215* (2006.01)

(52) U.S. Cl.
CPC ........ *A61B 5/6851* (2013.01); *A61B 5/02154* (2013.01); *A61B 5/6852* (2013.01); *A61B 2562/0233* (2013.01)

(58) Field of Classification Search
CPC ........ A61B 2562/0233; A61B 5/02154; A61B 5/6851; A61B 5/6852
See application file for complete search history.

(56) References Cited

U.S. PATENT DOCUMENTS

| | | |
|---|---|---|
| 3,963,323 A | 6/1976 | Arnold |
| 4,771,782 A | 9/1988 | Millar |
| 4,953,553 A | 9/1990 | Tremulis |
| 5,106,455 A | 4/1992 | Jacobsen et al. |
| 5,178,159 A | 1/1993 | Christian |
| 5,238,004 A | 8/1993 | Sahatjian et al. |
| 5,313,957 A | 5/1994 | Little |
| 5,421,195 A | 6/1995 | Wlodarczyk |
| 5,422,969 A | 6/1995 | Eno |
| 5,427,114 A | 6/1995 | Colliver et al. |
| 5,438,873 A | 8/1995 | Wlodarczyk et al. |
| 5,573,520 A | 11/1996 | Schwartz et al. |
| 5,633,963 A | 5/1997 | Rickenbach et al. |
| 5,755,668 A | 5/1998 | Itoigawa et al. |
| 5,772,609 A | 6/1998 | Nguyen et al. |
| 5,797,856 A | 8/1998 | Frisbie et al. |

(Continued)

FOREIGN PATENT DOCUMENTS

| | | |
|---|---|---|
| DE | 202014100938 U1 | 3/2014 |
| EP | 0235992 A1 | 9/1987 |

(Continued)

*Primary Examiner* — Amanda Patton
(74) *Attorney, Agent, or Firm* — Seager, Tufte & Wickhem, LLP (57) ABSTRACT

Medical devices and methods for making and using medical devices are disclosed. An example medical device may include a medical device for measuring blood pressure. The medical device may include an elongated shaft having a proximal region and a distal region. An optical fiber may extend along the proximal region. An optical pressure sensor may be coupled to the optical fiber. The optical pressure sensor may be disposed along the distal region. A centering member may be coupled to the optical fiber and positioned adjacent to the optical pressure sensor.

20 Claims, 6 Drawing Sheets

(56) References Cited

U.S. PATENT DOCUMENTS

| | | |
|---|---|---|
| 5,872,879 A | 2/1999 | Hamm |
| 5,902,248 A | 5/1999 | Millar et al. |
| 5,938,624 A | 8/1999 | Akerfeldt et al. |
| 5,949,929 A | 9/1999 | Hamm |
| 6,112,598 A | 9/2000 | Tenerz et al. |
| 6,120,457 A | 9/2000 | Coombes et al. |
| 6,139,510 A | 10/2000 | Palermo |
| 6,162,182 A | 12/2000 | Cole |
| 6,167,763 B1 | 1/2001 | Tenerz et al. |
| 6,196,980 B1 | 3/2001 | Akerfeldt et al. |
| 6,248,083 B1 | 6/2001 | Smith et al. |
| 6,265,792 B1 | 7/2001 | Granchukoff |
| 6,394,986 B1 | 5/2002 | Millar |
| 6,398,738 B1 | 6/2002 | Millar |
| 6,409,677 B1 | 6/2002 | Tulkki |
| 6,428,336 B1 | 8/2002 | Akerfeldt |
| 6,508,803 B1 | 1/2003 | Horikawa et al. |
| 6,565,514 B2 | 5/2003 | Svanerudh et al. |
| 6,579,246 B2 | 6/2003 | Jacobsen et al. |
| 6,585,660 B2 | 7/2003 | Dorando et al. |
| 6,615,067 B2 | 9/2003 | Hoek et al. |
| 6,663,570 B2 | 12/2003 | Mott et al. |
| 6,766,720 B1 | 7/2004 | Jacobsen et al. |
| 6,767,327 B1 | 7/2004 | Corl et al. |
| 6,776,720 B2 | 8/2004 | Bartlett |
| 6,908,442 B2 | 6/2005 | von Malmborg et al. |
| 6,918,873 B1 | 7/2005 | Millar et al. |
| 6,918,882 B2 | 7/2005 | Skujins et al. |
| 6,974,422 B1 | 12/2005 | Millar |
| 6,976,965 B2 | 12/2005 | Corl et al. |
| 6,993,974 B2 | 2/2006 | Tenerz et al. |
| 6,994,695 B1 | 2/2006 | Millar |
| 7,071,197 B2 | 7/2006 | Leonardi et al. |
| 7,134,994 B2 | 11/2006 | Alpert et al. |
| 7,162,926 B1 | 1/2007 | Guziak et al. |
| 7,187,453 B2 | 3/2007 | Belleville |
| 7,259,862 B2 | 8/2007 | Duplain |
| 7,265,847 B2 | 9/2007 | Duplain et al. |
| 7,274,956 B2 | 9/2007 | Mott et al. |
| 7,331,236 B2 | 2/2008 | Smith et al. |
| 7,532,920 B1 | 5/2009 | Ainsworth et al. |
| 7,618,379 B2 | 11/2009 | Reynolds et al. |
| 7,684,657 B2 | 3/2010 | Donlagic et al. |
| 7,689,071 B2 | 3/2010 | Belleville et al. |
| 7,715,903 B2 | 5/2010 | Hartley et al. |
| 7,724,148 B2 | 5/2010 | Samuelsson et al. |
| 7,731,664 B1 | 6/2010 | Millar |
| 7,759,633 B2 | 7/2010 | Duplain et al. |
| 7,783,338 B2 | 8/2010 | Ainsworth et al. |
| 7,878,984 B2 | 2/2011 | Jacobsen et al. |
| 7,930,014 B2 | 4/2011 | Huennekens et al. |
| 7,946,997 B2 | 5/2011 | Hübinette |
| 8,025,623 B1 | 9/2011 | Millar |
| 8,029,447 B2 | 10/2011 | Kanz et al. |
| 8,174,395 B2 | 5/2012 | Samuelsson et al. |
| 8,216,151 B2 | 7/2012 | Smith |
| 8,298,156 B2 | 10/2012 | Manstrom et al. |
| 8,317,715 B2 | 11/2012 | Belleville et al. |
| 8,343,076 B2 * | 1/2013 | Sela .......... A61B 5/06 600/410 |
| 8,393,802 B2 | 3/2013 | Stanley et al. |
| 8,410,940 B2 | 4/2013 | Samuelsson et al. |
| 8,461,997 B2 | 6/2013 | Samuelsson et al. |
| 8,485,985 B2 | 7/2013 | Manstrom et al. |
| 8,555,712 B2 | 10/2013 | Narvaez et al. |
| 8,556,820 B2 | 10/2013 | Alpert et al. |
| 8,562,537 B2 | 10/2013 | Alpert et al. |
| 8,583,218 B2 | 11/2013 | Eberle |
| 8,636,659 B2 | 1/2014 | Alpert et al. |
| 8,641,633 B2 | 2/2014 | Smith |
| 8,641,639 B2 | 2/2014 | Manstrom et al. |
| 8,676,299 B2 | 3/2014 | Schmitt et al. |
| 8,698,638 B2 | 4/2014 | Samuelsson et al. |
| 8,752,435 B2 | 6/2014 | Belleville et al. |
| 8,936,401 B2 | 1/2015 | Belleville et al. |
| 8,998,823 B2 | 4/2015 | Manstrom et al. |
| 9,052,466 B2 | 6/2015 | Belleville et al. |
| 2003/0069522 A1 | 4/2003 | Jacobsen et al. |
| 2004/0073141 A1 | 4/2004 | Hartley et al. |
| 2004/0181174 A2 | 9/2004 | Davis et al. |
| 2005/0000294 A1 | 1/2005 | Tenerz et al. |
| 2006/0122537 A1 | 6/2006 | Reynolds et al. |
| 2008/0119758 A1 | 5/2008 | Samuelsson et al. |
| 2009/0082678 A1 | 3/2009 | Smith |
| 2009/0192412 A1 | 7/2009 | Sela et al. |
| 2010/0145308 A1 | 6/2010 | Layman et al. |
| 2010/0241008 A1 | 9/2010 | Belleville et al. |
| 2011/0071407 A1 | 3/2011 | Hübinette et al. |
| 2011/0178413 A1 | 7/2011 | Schmitt et al. |
| 2011/0186294 A1 | 8/2011 | Narvaez et al. |
| 2011/0319773 A1 | 12/2011 | Kanz et al. |
| 2012/0227505 A1 | 9/2012 | Belleville et al. |
| 2012/0265102 A1 | 10/2012 | Leo et al. |
| 2013/0051731 A1 | 2/2013 | Belleville et al. |
| 2013/0218032 A1* | 8/2013 | Belleville .......... A61M 25/09 600/486 |
| 2013/0296718 A1 | 11/2013 | Ranganathan et al. |
| 2013/0317372 A1 | 11/2013 | Eberle et al. |
| 2014/0005558 A1 | 1/2014 | Gregorich |
| 2014/0058275 A1* | 2/2014 | Gregorich .......... A61B 5/02141 600/485 |
| 2014/0081244 A1 | 3/2014 | Voeller et al. |
| 2014/0107624 A1 | 4/2014 | Belleville |
| 2014/0121475 A1 | 5/2014 | Alpert et al. |
| 2014/0241669 A1 | 8/2014 | Belleville et al. |
| 2014/0248021 A1 | 9/2014 | Belleville et al. |
| 2015/0301288 A1 | 10/2015 | Thornton, Jr. |

FOREIGN PATENT DOCUMENTS

| | | |
|---|---|---|
| EP | 0738495 A1 | 10/1996 |
| EP | 0879615 A1 | 11/1998 |
| EP | 0879617 A1 | 11/1998 |
| EP | 1479407 A1 | 11/2004 |
| WO | 9313707 A1 | 7/1993 |
| WO | 9533983 A1 | 12/1995 |
| WO | 9945352 A1 | 9/1999 |
| WO | 2008034010 A2 | 3/2008 |
| WO | 2011027282 A1 | 3/2011 |
| WO | 2011090744 A2 | 7/2011 |
| WO | 2011123689 A1 | 10/2011 |
| WO | 2012000798 A1 | 1/2012 |
| WO | 2012090210 A1 | 7/2012 |
| WO | 2013033489 A1 | 3/2013 |
| WO | 2014025255 A1 | 2/2014 |

* cited by examiner

PRESSURE SENSING GUIDEWIRES

CROSS-REFERENCE TO RELATED APPLICATIONS

This application claims priority under 35 U.S.C. §119 to U.S. Provisional Application Ser. No. 62/032,169, filed Aug. 1, 2014, the entirety of which is incorporated herein by reference.

TECHNICAL FIELD

The present disclosure pertains to medical devices, and methods for manufacturing medical devices. More particularly, the present disclosure pertains to blood pressure sensing guidewires and methods for using pressure sensing guidewires.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example medical device for measuring blood pressure includes an elongated shaft having a proximal region and a distal region. An optical fiber extends along the proximal region. An optical pressure sensor is coupled to the optical fiber. The optical pressure sensor is disposed along the distal region. A centering member is coupled to the optical fiber and positioned adjacent to the optical pressure sensor.

Alternatively or additionally to any of the examples above, in another example, the centering member may include a polymer.

Alternatively or additionally to any of the examples above, in another example, the centering member has a substantially circular cross-sectional shape.

Alternatively or additionally to any of the examples above, in another example, the centering member has a non-circular cross-sectional shape.

Alternatively or additionally to any of the examples above, in another example, the centering member includes a coil.

Alternatively or additionally to any of the examples above, in another example, the centering member is disposed at a proximal end of the optical pressure sensor.

Alternatively or additionally to any of the examples above, in another example, the centering member is spaced from a proximal end of the optical pressure sensor.

Alternatively or additionally to any of the examples above, in another example, the shaft has a plurality of slots formed therein.

Alternatively or additionally to any of the examples above, in another example, at least some of the slots are positioned adjacent to the centering member.

Alternatively or additionally to any of the examples above, in another example, the distal region has a distal inner diameter, wherein the proximal region has a proximal inner diameter, and wherein the distal inner diameter is greater than the proximal inner diameter.

Alternatively or additionally to any of the examples above, the distal region of the shaft has a distal inner diameter, wherein the proximal region of the shaft has a proximal inner diameter, and wherein the distal inner diameter is larger than the proximal inner diameter.

Alternatively or additionally to any of the examples above, the centering member is disposed within the shaft along the distal region.

Alternatively or additionally to any of the examples above, the centering member is coupled to an outer surface of the optical fiber.

Alternatively or additionally to any of the examples above, the centering member is coupled to an inner surface of the distal region of the shaft.

Alternatively or additionally to any of the examples above, the medical device is a guidewire for measuring fractional flow reserve.

An example pressure sensing guidewire includes a tubular member having a proximal region and a distal region. The distal region has a distal inner diameter. The proximal region has a proximal inner diameter. The distal inner diameter is larger than the proximal inner diameter. An optical fiber extends within the tubular member along the proximal region. An optical pressure sensor is coupled to the optical fiber. The optical pressure sensor is disposed within the tubular member along the distal region. A centering member is disposed within the tubular member along the distal region. The centering member is coupled to an outer surface of the optical fiber. The centering member is coupled to an inner surface of the distal region of the tubular member.

Alternatively or additionally to any of the examples above, in another example, the centering member includes a coil.

Alternatively or additionally to any of the examples above, in another example, the centering member is disposed at a proximal end of the optical pressure sensor.

Alternatively or additionally to any of the examples above, in another example, the centering member is spaced from a proximal end of the optical pressure sensor.

Alternatively or additionally to any of the examples above, in another example, the shaft has a plurality of slots formed therein and wherein at least some of the slots are positioned adjacent to the centering member.

An example medical device for measuring blood pressure includes an elongated shaft having a proximal region and a distal region. An optical fiber extends along the proximal region. An optical pressure sensor is coupled to the optical fiber. The optical pressure sensor is disposed along the distal region. A centering member is coupled to the optical fiber and positioned adjacent to the optical pressure sensor.

Alternatively or additionally to any of the examples above, in another example, the centering member includes a polymer.

Alternatively or additionally to any of the examples above, in another example, the centering member has a substantially circular cross-sectional shape.

Alternatively or additionally to any of the examples above, in another example, the centering member has a non-circular cross-sectional shape.

Alternatively or additionally to any of the examples above, in another example, the centering member includes a coil.

Alternatively or additionally to any of the examples above, in another example, the centering member is disposed at a proximal end of the optical pressure sensor.

Alternatively or additionally to any of the examples above, in another example, the centering member is spaced from a proximal end of the optical pressure sensor. Alternatively or additionally to any of the examples above, in another example, the shaft has a plurality of slots formed therein.

Alternatively or additionally to any of the examples above, in another example, at least some of the slots are positioned adjacent to the centering member.

Alternatively or additionally to any of the examples above, in another example, the distal region has a distal inner diameter, wherein the proximal region has a proximal inner diameter, and wherein the distal inner diameter is greater than the proximal inner diameter.

An example pressure sensing guidewire includes a tubular member having a proximal region and a distal region. The distal region has a distal inner diameter. The proximal region has a proximal inner diameter. The distal inner diameter is larger than the proximal inner diameter. An optical fiber extends within the tubular member along the proximal region. An optical pressure sensor is coupled to the optical fiber. The optical pressure sensor is disposed within the tubular member along the distal region. A centering member is disposed within the tubular member along the distal region. The centering member is coupled to an outer surface of the optical fiber. The centering member is coupled to an inner surface of the distal region of the tubular member.

Alternatively or additionally to any of the examples above, in another example, the centering member includes a polymer.

Alternatively or additionally to any of the examples above, in another example, the centering member has a substantially circular cross-sectional shape.

Alternatively or additionally to any of the examples above, in another example, the centering member has a non-circular cross-sectional shape.

Alternatively or additionally to any of the examples above, in another example, the centering member includes a coil.

Alternatively or additionally to any of the examples above, in another example, the centering member is disposed at a proximal end of the optical pressure sensor.

Alternatively or additionally to any of the examples above, in another example, the centering member is spaced from a proximal end of the optical pressure sensor.

Alternatively or additionally to any of the examples above, in another example, the shaft has a plurality of slots formed therein.

Alternatively or additionally to any of the examples above, in another example, at least some of the slots are positioned adjacent to the centering member.

A pressure sensing guidewire for measuring fractional flow reserve includes an elongate shaft having a proximal region and a distal region. The distal region has a distal inner diameter. The proximal region has a proximal inner diameter that is smaller than the distal inner diameter. The distal region has a plurality of slots formed therein. An optical fiber extends within the shaft along the proximal region. An optical pressure sensor is coupled to the optical fiber. The optical pressure sensor is disposed within the distal region of the shaft. A centering member is coupled to the optical fiber. The centering member is designed to reduce contact between an inner surface of the shaft and the optical pressure sensor.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

During some medical interventions, it may be desirable to measure and/or monitor the blood pressure within a blood vessel. For example, some medical devices may include pressure sensors that allow a clinician to monitor blood pressure. Such devices may be useful in determining fractional flow reserve (FFR), which may be understood as the pressure after a stenosis relative to the pressure before the stenosis (and/or the aortic pressure).

Figure 1:
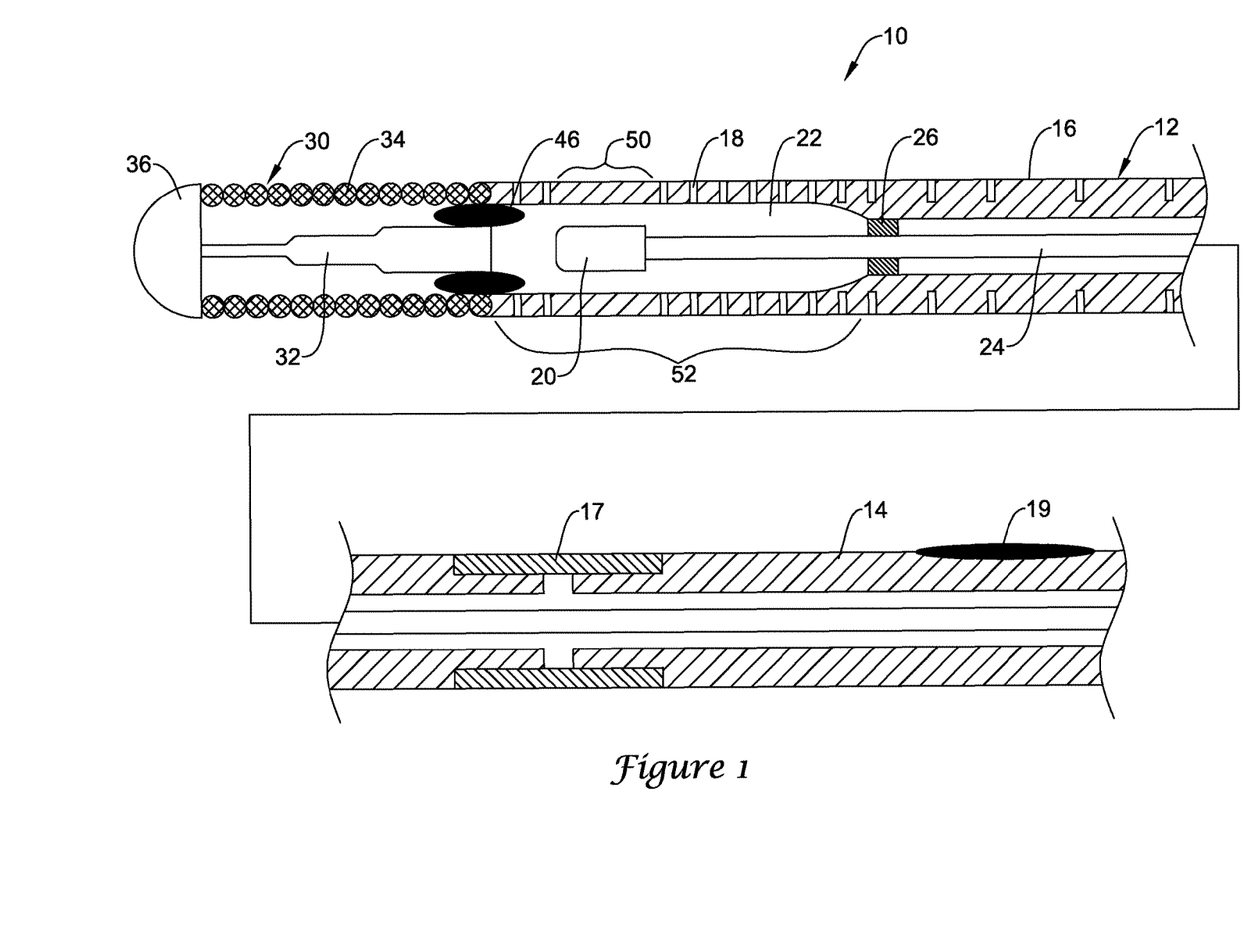
FIG. 1 is a partial cross-sectional side view of a portion of an example medical device.

FIG. 1 illustrates a portion of an example medical device 10. In this example, medical device 10 is a blood pressure sensing guidewire 10. However, this is not intended to be limiting as other medical devices are contemplated including, for example, catheters, shafts, leads, wires, or the like. Guidewire 10 may include a tubular member or shaft 12. Shaft 12 may include a proximal portion 14 and a distal portion 16. The materials for proximal portion 14 and distal portion 16 may vary and may include those materials disclosed herein. For example, distal portion 16 may include a nickel-cobalt-chromium-molybdenum alloy (e.g., MP35-N). Proximal portion 14 may include stainless steel. These are just examples. Other materials may also be utilized.

In some embodiments, proximal portion 14 and distal portion 16 are formed from the same monolith of material. In other words, proximal portion 14 and distal portion 16 are portions of the same tube defining shaft 12. In other embodiments, proximal portion 14 and distal portion 16 are separate tubular members that are joined together. For example, a section of the outer surface of portions 14/16 may be removed and a sleeve 17 may be disposed over the removed sections to join portions 14/16. Alternatively, sleeve 17 may be simply disposed over portions 14/16. Other bonds may also be used including welds, thermal bonds, adhesive bonds, or the like. If utilized, sleeve 17 used to join proximal portion 14 with distal portion 16 may include a material that desirably bonds with both proximal portion 14 and distal portion 16. For example, sleeve 17 may include a nickel-chromium-molybdenum alloy (e.g., INCONEL).

A plurality of slots 18 may be formed in shaft 12. In at least some embodiments, slots 18 are formed in distal portion 16. In at least some embodiments, proximal portion 14 lacks slots 18. However, proximal portion 14 may include slots 18. Slots 18 may be desirable for a number of reasons. For example, slots 18 may provide a desirable level of flexibility to shaft 12 (e.g., along distal portion 16) while also allowing suitable transmission of torque. Slots 18 may be arranged/distributed along distal portion 16 in a suitable manner including any of those arrangements disclosed herein. For example, slots 18 may be arranged as opposing pairs of slots 18 that are distributed along the length of distal portion 16. In some embodiments, adjacent pairs of slots 18 may have a substantially constant spacing relative to one another. Alternatively, the spacing between adjacent pairs may vary. For example, more distal regions of distal portion 16 may have a decreased spacing (and/or increased slot density), which may provide increased flexibility. In other embodiments, more distal regions of distal portion 16 may have an increased spacing (and/or decreased slot density). These are just examples. Other arrangements are contemplated.

A pressure sensor 20 may be disposed within shaft 12 (e.g., within a lumen 22 of shaft 12). While pressure sensor 20 is shown schematically in FIG. 1, it can be appreciated that the structural form and/or type of pressure sensor 20 may vary. For example, pressure sensor 20 may include a semiconductor (e.g., silicon wafer) pressure sensor, piezo-electric pressure sensor, a fiber optic or optical pressure sensor, a Fabry-Perot type pressure sensor, an ultrasound transducer and/or ultrasound pressure sensor, a magnetic pressure sensor, a solid-state pressure sensor, or the like, or any other suitable pressure sensor.

As indicated above, pressure sensor 20 may include an optical pressure sensor. In at least some of these embodiments, an optical fiber or fiber optic cable 24 (e.g., a multimode fiber optic) may be attached to pressure sensor 20 and may extend proximally therefrom. An attachment member 26 may attach optical fiber 24 to shaft 12. Attachment member 26 may be circumferentially disposed about and attached to optical fiber 24 and may be secured to the inner surface of shaft 12 (e.g., distal portion 16). In at least some embodiments, attachment member 26 is proximally spaced from pressure sensor 20. Other arrangements are contemplated.

In at least some embodiments, distal portion 16 may include a region with a thinned wall and/or an increased inner diameter that defines a housing region 52. In general, housing region 52 is the region of distal portion 16 that ultimately "houses" the pressure sensor (e.g., pressure sensor 20). By virtue of having a portion of the inner wall of shaft 12 being removed at housing region 52, additional space may be created or otherwise defined that can accommodate sensor 20.

In at least some embodiments, it may be desirable for pressure sensor 20 to have reduced exposure along its side surfaces to fluid pressure (e.g., from the blood). Accordingly, it may be desirable to position pressure sensor 20 along a landing region 50 defined along housing region 52. Landing region 50 may be substantially free of slots 18 so that the side surfaces of pressure sensor 20 have a reduced likelihood of being deformed due to fluid pressures at these locations. Distal of landing region 50, housing region 52 may include slots 18 that provide fluid access to pressure sensor 20.

Moreover, one or more of slots 18 may define a fluid pathway that allows blood (and/or a body fluid) to flow from a position along the exterior or outer surface of guidewire 10 (and/or shaft 12), through slots 18, and into the lumen 22 of shaft 12, where the blood can come into contact with pressure sensor 20. Because of this, no additional side openings/holes (e.g., other than one or more slots 18, a single slot 18 extending through the wall of shaft 12, and/or a dedicated pressure port or opening) may be necessary in shaft 12 for pressure measurement. This may also allow the length of distal portion 16 to be shorter than typical sensor mounts or hypotubes that would need to have a length sufficient for a suitable opening/hole (e.g., a suitable "large" opening/hole) to be formed therein that provides fluid access to sensor 20.

A tip member 30 may be coupled to distal portion 16. Tip member 30 may include a shaping member 32 and a spring or coil member 34. A distal tip 36 may be attached to shaping member 32 and/or spring 34. In at least some embodiments, distal tip 36 may take the form of a solder ball tip. Tip member 30 may be joined to distal portion 16 of shaft 12 with a bonding member 46 such as a weld.

Shaft 12 may include a hydrophilic coating 19. In some embodiments, hydrophilic coating 19 may extend along substantially the full length of shaft 12. In other embodiments, one or more discrete sections of shaft 12 may include hydrophilic coating 19.

Figure 2:
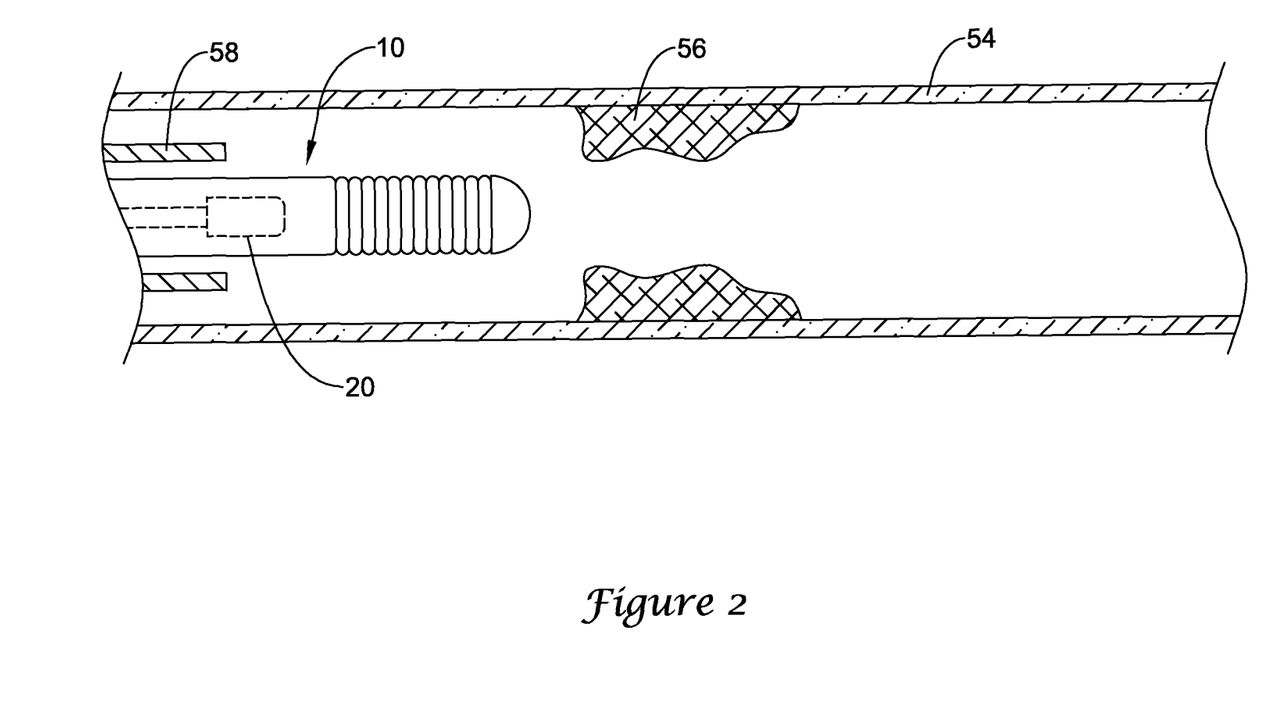
FIG. 2 is a partial cross-sectional view of an example medical device disposed at a first position adjacent to an intravascular occlusion.
Figure 3:
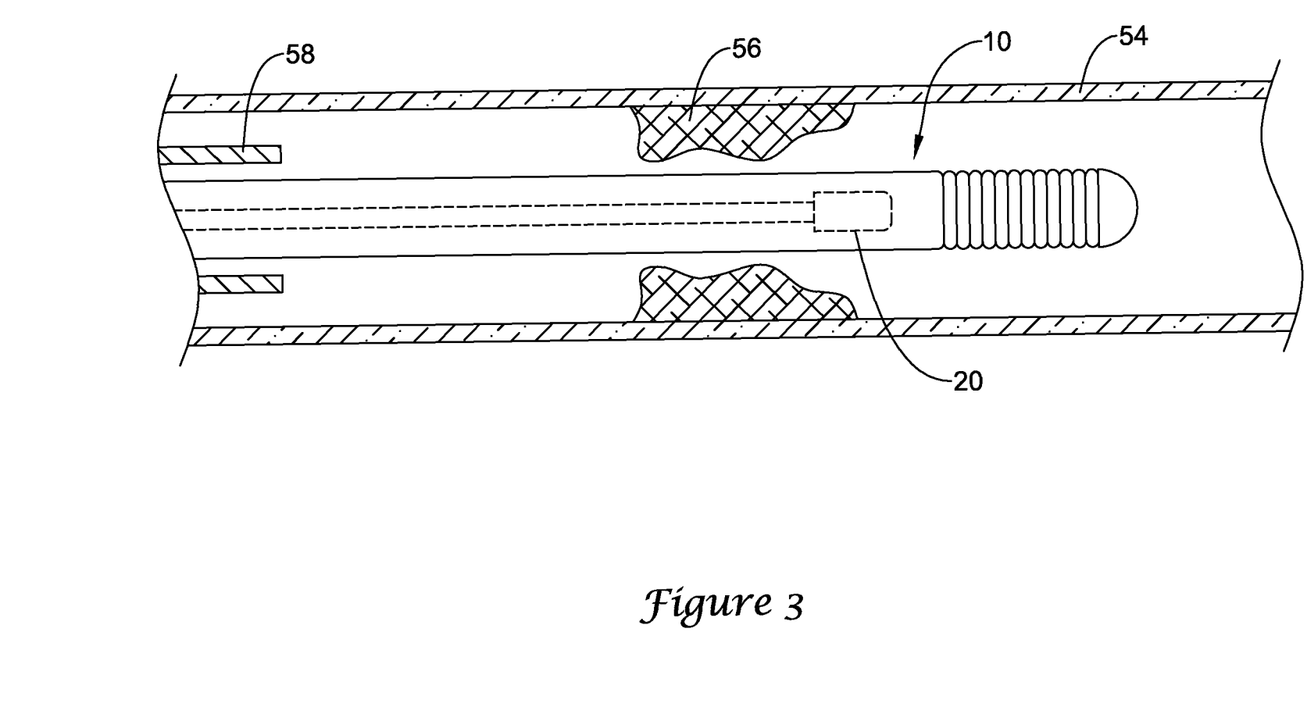
FIG. 3 is a partial cross-sectional view of an example medical device disposed at a second position adjacent to an intravascular occlusion.

In use, a clinician may use guidewire 10 to measure and/or calculate FFR (e.g., the pressure after an intravascular occlusion relative to the pressure before the occlusion and/or the aortic pressure). Measuring and/or calculating FFR may include measuring the aortic pressure in a patient. This may include advancing guidewire 10 through a blood vessel or body lumen 54 to a position that is proximal or upstream of an occlusion 56 as shown in FIG. 2. For example, guidewire 10 may be advanced through a guide catheter 58 to a position where at least a portion of sensor 20 is disposed distal of the distal end of guide catheter 58 and measuring the pressure within body lumen 54. This pressure may be characterized as an initial pressure. In some embodiments, the aortic pressure may also be measured by another device (e.g., a pressure sensing guidewire, catheter, or the like). The initial pressure may be equalized with the aortic pressure. For example, the initial pressure measured by guidewire 10 may be set to be the same as the measured aortic pressure. Guidewire 10 may be further advanced to a position distal or downstream of occlusion 56 as shown in FIG. 3 and the pressure within body lumen 54 may be measured. This pressure may be characterized as the downstream or distal pressure. The distal pressure and the aortic pressure may be used to calculate FFR.

It can be appreciated that an FFR system that utilizes an optical pressure sensor in a pressure sensing guidewire may be navigated through the tortuous anatomy. This may include crossing relatively tight bends in the vasculature. Because of this, and for other reasons, it may be desirable of pressure sensing guidewire to be relatively flexible, for example adjacent to the distal end. It can be appreciated that in relatively flexible guidewires, bending the guidewire could result in contact between an inner surface of the guidewire and, for example, the pressure sensor. Such contact could lead to alterations and/or deformations of the pressure sensor, potentially leading to pressure reading offsets. Disclosed herein are pressure-sensing guidewires with increased flexibility. Furthermore, the guidewires disclosed herein may also include structural features that may help to reduce contact between the pressure sensor and the inner surface of the guidewire and, therefore, help to reduce the possibility of pressure reading offsets.

Figure 4:
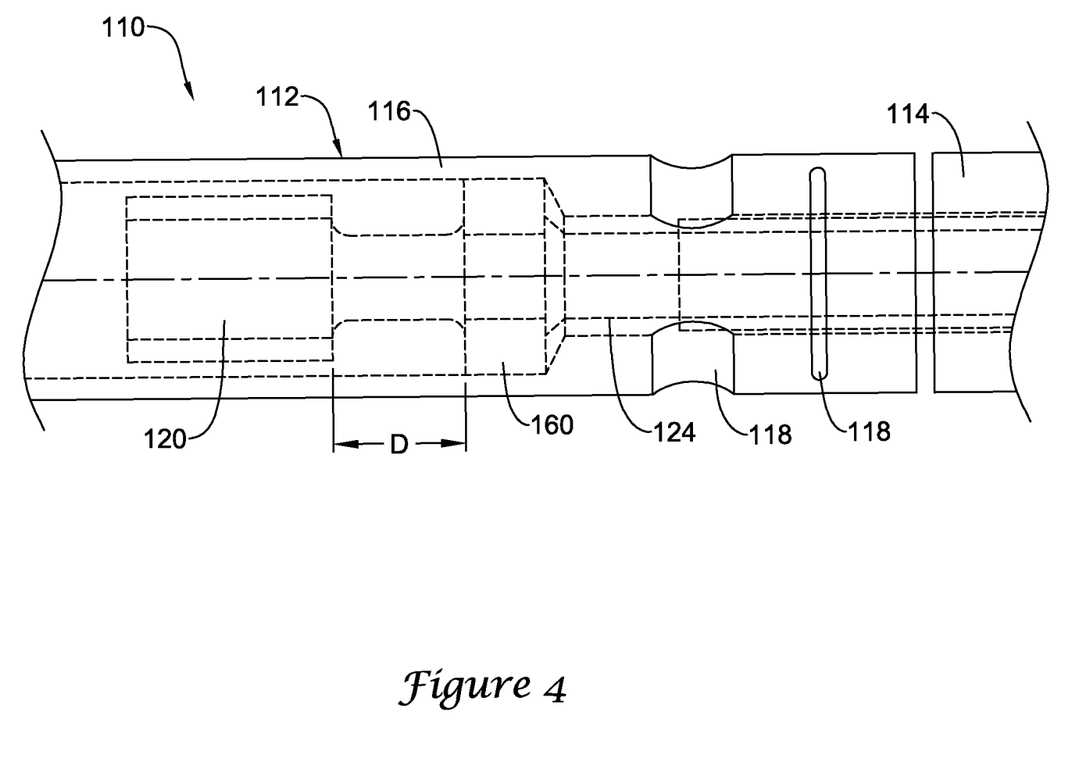
FIG. 4 is a partial cross-sectional side view of a portion of an example medical device.

FIG. 4 illustrates a portion of another example guidewire 110 that may be similar in form and function to other guidewires disclosed herein. Guidewire 110 may include shaft 112 having proximal portion 114 and distal portion 116. Distal portion 116 may have slots or slits 118 formed therein. At least some of slits 118 may extend through only a portion of the wall of shaft 112. Pressure sensor 120 may be disposed within shaft 112. In at least some embodiments, pressure sensor 120 may be an optical pressure sensor having optical fiber 124 coupled thereto.

A centering member 160 may be coupled to optical fiber 124. In general, centering member 160 may be disposed along distal portion 116 of shaft 112 and may define a location where contact may occur with the inner surface of shaft 112. More particularly, when shaft 112 is bent, deflected, or otherwise deformed, the outer surface of centering member 160 may come into contact with the inner surface of shaft 112. In doing so, centering member 160 may reduce the likelihood that inner surface of shaft 112 may contact pressure sensor 120. Therefore, by including centering member 160, guidewire 110 may be less likely to have pressure reading offsets.

In at least some embodiments, centering member 160 may be positioned adjacent to pressure sensor 120. For example, centering member 160 may be spaced a distance D from the proximal end of pressure sensor 120. Distance D may be on the order of about 1-20 mm, or about 1-10 mm, or about 1-5 mm. These are just examples. Other distances are contemplated. In other embodiments, centering member 160 may be positioned adjacent the distal end of pressure sensor 120.

The form of centering member 160 may vary. In some instances, centering member 160 may be a polymer member coupled to optical fiber 124. The polymer may include any of the polymers disclosed herein (e.g., polyimide). The shape or form of centering member 160 may also vary. For example, centering member 160 may take the form of a cylindrical disk coupled to optical fiber 124. However, a number of other shapes, lengths, and forms are contemplated. This may include centering members 160 with a substantially circular cross-sectional shape, with a non-circular cross-sectional shape, or the like. The number of centering members 160 may also vary. In some embodiments, only one centering member 160 may be utilized. In other embodiments, two, three, four, five, six, or more centering members 160 may be utilized. The centering member(s) 160 may be arranged in a variety of different locations (proximal, distal, immediately adjacent, etc.) relative to pressure sensor 120.

Figure 5:
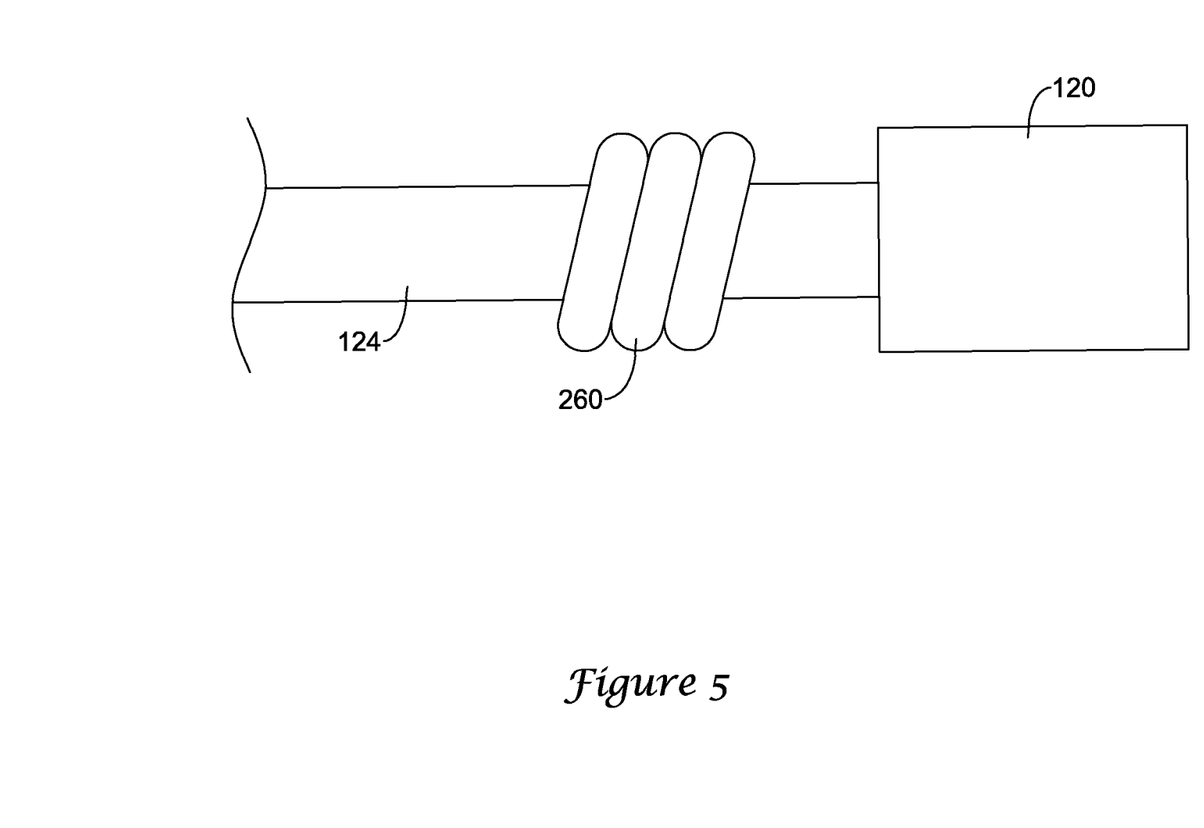
FIG. 5 is side view of a portion of an example medical device.

FIG. 5 illustrates another example centering member 260 taking the form of a coil. The form of the coil may also vary. For example, the coil may have an open pitch (e.g., with space between adjacent coil windings), a closed pitch (e.g., where adjacent coil winding contact one another), or combinations thereof. In some instances, more than one coiled centering member 260 may be utilized.

Figure 6:
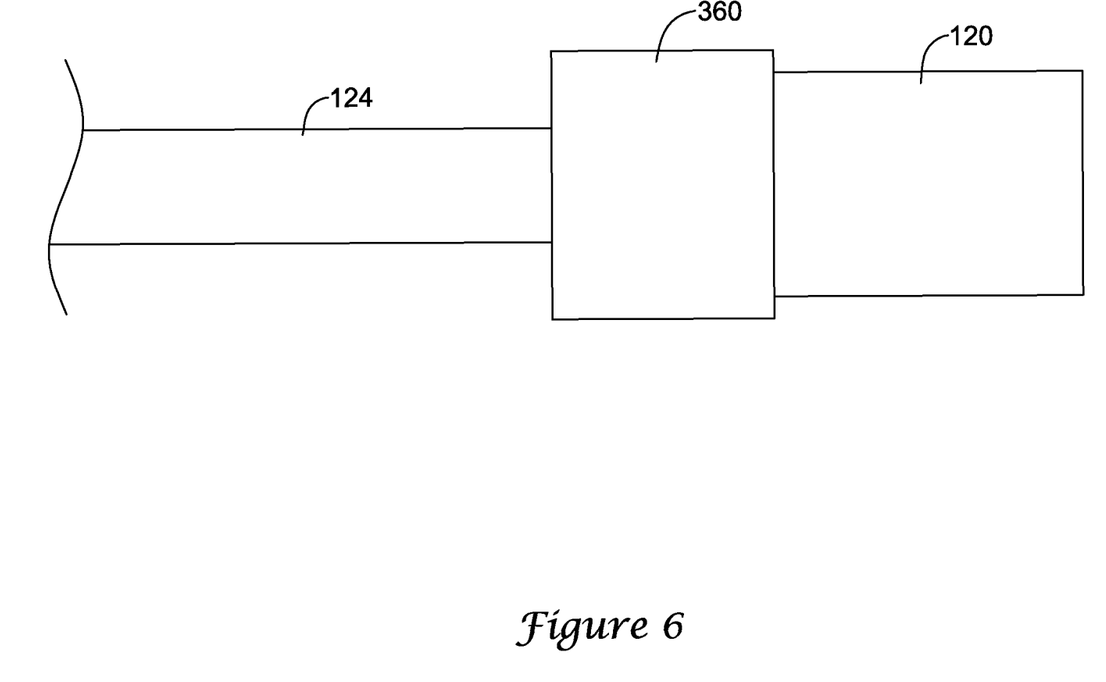
FIG. 6 is side view of a portion of an example medical device.

While FIGS. 4-5 illustrate centering member 160/260 as being spaced from, for example, a proximal end of pressure sensor 120, this is not intended to be limiting. For example, FIG. 6 illustrates another example centering member 360 that is positioned directly adjacent to pressure sensor 120. In this example, pressure sensor 120 is positioned against pressure sensor 120.

The materials that can be used for the various components of guidewire 10 (and/or other guidewires disclosed herein) and the various tubular members disclosed herein may include those commonly associated with medical devices. For simplicity purposes, the following discussion makes reference to shaft 12 and other components of guidewire 10. However, this is not intended to limit the devices and methods described herein, as the discussion may be applied to other tubular members and/or components of tubular members or devices disclosed herein.

Shaft 12 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® UNS: N10276 such as HASTELLOY® C276®), other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of guidewire 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of guidewire 10 to achieve the same result.

In some embodiments, a degree of Magnetic Resonance Imaging (MRI) compatibility is imparted into guidewire 10. For example, shaft 12 or portions thereof may be made of a material that does not substantially distort the image and create substantial artifacts (i.e., gaps in the image). Certain ferromagnetic materials, for example, may not be suitable because they may create artifacts in an MRI image. Shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

A sheath or covering (not shown) may be disposed over portions or all of shaft 12 that may define a generally smooth outer surface for guidewire 10. In other embodiments, however, such a sheath or covering may be absent from a portion of all of guidewire 10, such that shaft 12 may form the outer surface. The sheath may be made from a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b- styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the exterior surface of the guidewire 10 (including, for example, the exterior surface of shaft 12) may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the sheath, or in embodiments without a sheath over portion of shaft 12, or other portions of guidewire 10. Alternatively, the sheath may comprise a lubricious, hydrophilic, protective, or other type of coating. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Various embodiments of arrangements and configurations of slots are also contemplated that may be used in addition to what is described above or may be used in alternate embodiments. For simplicity purposes, the following disclosure makes reference to guidewire 10, slots 18, and shaft 12. However, it can be appreciated that these variations may also be utilized for other slots and/or tubular members. In some embodiments, at least some, if not all of slots 18 are disposed at the same or a similar angle with respect to the longitudinal axis of shaft 12. As shown, slots 18 can be disposed at an angle that is perpendicular, or substantially perpendicular, and/or can be characterized as being disposed in a plane that is normal to the longitudinal axis of shaft 12. However, in other embodiments, slots 18 can be disposed at an angle that is not perpendicular, and/or can be characterized as being disposed in a plane that is not normal to the longitudinal axis of shaft 12. Additionally, a group of one or more slots 18 may be disposed at different angles relative to another group of one or more slots 18. The distribution and/or configuration of slots 18 can also include, to the extent applicable, any of those disclosed in U.S. Pat. Publication No. US 2004/0181174, the entire disclosure of which is herein incorporated by reference.

Slots 18 may be provided to enhance the flexibility of shaft 12 while still allowing for suitable torque transmission characteristics. Slots 18 may be formed such that one or more rings and/or tube segments interconnected by one or more segments and/or beams that are formed in shaft 12, and such tube segments and beams may include portions of shaft 12 that remain after slots 18 are formed in the body of shaft 12. Such an interconnected structure may act to maintain a relatively high degree of torsional stiffness, while maintaining a desired level of lateral flexibility. In some embodiments, some adjacent slots 18 can be formed such that they include portions that overlap with each other about the circumference of shaft 12. In other embodiments, some adjacent slots 18 can be disposed such that they do not necessarily overlap with each other, but are disposed in a pattern that provides the desired degree of lateral flexibility.

Additionally, slots 18 can be arranged along the length of, or about the circumference of, shaft 12 to achieve desired properties. For example, adjacent slots 18, or groups of slots 18, can be arranged in a symmetrical pattern, such as being disposed essentially equally on opposite sides about the circumference of shaft 12, or can be rotated by an angle relative to each other about the axis of shaft 12. Additionally, adjacent slots 18, or groups of slots 18, may be equally spaced along the length of shaft 12, or can be arranged in an increasing or decreasing density pattern, or can be arranged in a non-symmetric or irregular pattern. Other characteristics, such as slot size, slot shape, and/or slot angle with respect to the longitudinal axis of shaft 12, can also be varied along the length of shaft 12 in order to vary the flexibility or other properties. In other embodiments, moreover, it is contemplated that the portions of the tubular member, such as a proximal section, or a distal section, or the entire shaft 12, may not include any such slots 18.

As suggested herein, slots 18 may be formed in groups of two, three, four, five, or more slots 18, which may be located at substantially the same location along the axis of shaft 12. Alternatively, a single slot 18 may be disposed at some or all of these locations. Within the groups of slots 18, there may be included slots 18 that are equal in size (i.e., span the same circumferential distance around shaft 12). In some of these as well as other embodiments, at least some slots 18 in a group are unequal in size (i.e., span a different circumferential distance around shaft 12). Longitudinally adjacent groups of slots 18 may have the same or different configurations. For example, some embodiments of shaft 12 include slots 18 that are equal in size in a first group and then unequally sized in an adjacent group. It can be appreciated that in groups that have two slots 18 that are equal in size and are symmetrically disposed around the tube circumference, the centroid of the pair of beams (i.e., the portion of shaft 12 remaining after slots 18 are formed therein) is coincident with the central axis of shaft 12. Conversely, in groups that have two slots 18 that are unequal in size and whose centroids are directly opposed on the tube circumference, the centroid of the pair of beams can be offset from the central axis of shaft 12. Some embodiments of shaft 12 include only slot groups with centroids that are coincident with the central axis of the shaft 12, only slot groups with centroids that are offset from the central axis of shaft 12, or slot groups with centroids that are coincident with the central axis of shaft 12 in a first group and offset from the central axis of shaft 12 in another group. The amount of offset may vary depending on the depth (or length) of slots 18 and can include other suitable distances.

Slots 18 can be formed by methods such as micromachining, saw-cutting (e.g., using a diamond grit embedded semiconductor dicing blade), electron discharge machining, grinding, milling, casting, molding, chemically etching or treating, or other known methods, and the like. In some such embodiments, the structure of the shaft 12 is formed by cutting and/or removing portions of the tube to form slots 18. Some example embodiments of appropriate micromachining methods and other cutting methods, and structures for tubular members including slots and medical devices including tubular members are disclosed in U.S. Pat. Publication Nos. 2003/0069522 and 2004/0181174-A2; and U.S. Pat. Nos. 6,766,720; and 6,579,246, the entire disclosures of which are herein incorporated by reference. Some example embodiments of etching processes are described in U.S. Pat. No. 5,106,455, the entire disclosure of which is herein incorporated by reference. It should be noted that the methods for manufacturing guidewire 110 may include forming slots 18 shaft 12 using these or other manufacturing steps.

In at least some embodiments, slots 18 may be formed in tubular member using a laser cutting process. The laser cutting process may include a suitable laser and/or laser cutting apparatus. For example, the laser cutting process may utilize a fiber laser. Utilizing processes like laser cutting may be desirable for a number of reasons. For example, laser cutting processes may allow shaft 12 to be cut into a number of different cutting patterns in a precisely controlled manner. This may include variations in the slot width, ring width, beam height and/or width, etc. Furthermore, changes to the cutting pattern can be made without the need to replace the cutting instrument (e.g., blade). This may also allow smaller tubes (e.g., having a smaller outer diameter) to be used to form shaft 12 without being limited by a minimum cutting blade size. Consequently, shaft 12 may be fabricated for use in neurological devices or other devices where a relatively small size may be desired.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A medical device for measuring blood pressure, comprising:
   an elongated shaft having a proximal region and a distal region;
   wherein the proximal region has a first wall thickness;
   wherein the distal region has a second wall thickness different from the first wall thickness;
   an optical fiber extending along the proximal region;
   an optical pressure sensor coupled to the optical fiber, the optical pressure sensor being disposed along the distal region; and
   a centering member coupled to the optical fiber and positioned within the distal region of the shaft at a position adjacent to the optical pressure sensor.

2. The medical device of claim 1, wherein the centering member includes a polymer.

3. The medical device of claim 1, wherein the centering member has a substantially circular cross-sectional shape.

4. The medical device of claim 1, wherein the centering member has a non-circular cross-sectional shape.

5. The medical device of claim 1, wherein the centering member includes a coil.

6. The medical device of claim 1, wherein the centering member is disposed at a proximal end of the optical pressure sensor.

7. The medical device of claim 1, wherein the centering member is spaced from a proximal end of the optical pressure sensor.

8. The medical device of claim 1, wherein the shaft has a plurality of slots formed therein.

9. The medical device of claim 8, wherein at least some of the slots are positioned adjacent to the centering member.

10. The medical device of claim 1, wherein the distal region has a distal inner diameter, wherein the proximal region has a proximal inner diameter, and wherein the distal inner diameter is greater than the proximal inner diameter.

11. A pressure sensing guidewire, comprising:
    a tubular member having a proximal region and a distal region;
    wherein the distal region has a distal inner diameter;
    wherein the proximal region has a proximal inner diameter;
    wherein the distal inner diameter is larger than the proximal inner diameter;
    an optical fiber extending within the tubular member along the proximal region;
    an optical pressure sensor coupled to the optical fiber, the optical pressure sensor being disposed within the tubular member along the distal region;
    a centering member disposed within the tubular member along the distal region;
    wherein the centering member is coupled to an outer surface of the optical fiber; and
    wherein the centering member is coupled to an inner surface of the distal region of the tubular member.

12. The guidewire of claim 11, wherein the centering member includes a polymer.

13. The guidewire of claim 11, wherein the centering member has a substantially circular cross-sectional shape.

14. The guidewire of claim 11, wherein the centering member has a non-circular cross-sectional shape.

15. The guidewire of claim 11, wherein the centering member includes a coil.

16. The guidewire of claim 11, wherein the centering member is disposed at a proximal end of the optical pressure sensor.

17. The guidewire of claim 11, wherein the centering member is spaced from a proximal end of the optical pressure sensor.

18. The guidewire of claim 11, wherein the shaft has a plurality of slots formed therein.

19. The guidewire of claim 18, wherein at least some of the slots are positioned adjacent to the centering member.

20. A pressure sensing guidewire for measuring fractional flow reserve, the guidewire comprising:
    an elongate shaft having a proximal region and a distal region;
    wherein the distal region has a distal inner diameter;
    wherein the proximal region has a proximal inner diameter that is smaller than the distal inner diameter;
    wherein the distal region has a plurality of slots formed therein;
    an optical fiber extending within the shaft along the proximal region;
    an optical pressure sensor coupled to the optical fiber, the optical pressure sensor being disposed within the distal region of the shaft; and a centering member coupled to the optical fiber and disposed within the distal region of the shaft, the centering member being designed to reduce contact between an inner surface of the shaft and the optical pressure sensor.

\* \* \* \* \*